(12) United States Patent
Weber

(10) Patent No.: US 8,721,861 B2
(45) Date of Patent: May 13, 2014

(54) METHOD FOR ELECTROPHORESIS INVOLVING PARALLEL AND SIMULTANEOUS SEPARATION

(75) Inventor: Gerhard Weber, Kirchheim (DE)

(73) Assignee: Becton, Dickinson and Company, Franklin Lakes, NJ (US)

(*) Notice: Subject to any disclaimer, the term of this patent is extended or adjusted under 35 U.S.C. 154(b) by 1258 days.

(21) Appl. No.: 11/912,612

(22) PCT Filed: Apr. 27, 2006

(86) PCT No.: PCT/US2006/016175
§ 371 (c)(1),
(2), (4) Date: Jun. 30, 2008

(87) PCT Pub. No.: WO2006/118996
PCT Pub. Date: Nov. 9, 2006

(65) Prior Publication Data
US 2009/0218224 A1 Sep. 3, 2009

(30) Foreign Application Priority Data
Apr. 29, 2005 (DE) .......................... 10 2005 020 134

(51) Int. Cl.
*G01N 27/447* (2006.01)
(52) U.S. Cl.
USPC ........................................................ 204/548
(58) Field of Classification Search
USPC ............... 204/450, 545, 548, 549; 205/777.5, 205/778, 792; 435/4–40.52, 28.1–288.77
See application file for complete search history.

(56) References Cited

U.S. PATENT DOCUMENTS

| | | |
|---|---|---|
| 2,555,487 A | 6/1951 | Haugaard et al. |
| 2,878,178 A | 3/1959 | Bier |
| 3,085,956 A | 4/1963 | Caplan |
| 3,125,500 A | 3/1964 | Grassman et al. |
| 3,140,714 A | 7/1964 | Murphy et al. |
| 3,149,060 A | 9/1964 | Dobry et al. |
| 3,287,244 A | 11/1966 | Mel |
| 3,320,148 A | 5/1967 | Skeggs |
| 3,320,149 A | 5/1967 | Isreeli |
| 3,412,007 A | 11/1968 | Strickler |
| 3,412,008 A | 11/1968 | Strickler |
| 3,458,427 A | 7/1969 | Strickler |
| 3,458,428 A | 7/1969 | Huebner |
| 3,498,905 A | 3/1970 | Strickler |
| 3,509,035 A | 4/1970 | Huebner |
| 3,519,549 A | 7/1970 | Grassman et al. |

(Continued)

FOREIGN PATENT DOCUMENTS

| | | |
|---|---|---|
| EP | 0081375 B1 | 6/1983 |
| JP | 061095241 A | 10/1984 |

(Continued)

OTHER PUBLICATIONS

Weber, G., et al., "Application of binary buffer systems to free flow cell electrophoresis", Electrophoresis, vol. 21, 2000, p. 325-328.*

(Continued)

*Primary Examiner* — J. Christopher Ball
(74) *Attorney, Agent, or Firm* — The Webb Law Firm

(57) ABSTRACT

An electrophoresis method is provided involving a parallel and simultaneous multiple process, using multiple separation sub-spaces within a separation chamber.

6 Claims, 3 Drawing Sheets

(56) References Cited

U.S. PATENT DOCUMENTS

| | | |
|---|---|---|
| 3,616,455 A | 10/1971 | Von Munchhausen |
| 3,655,541 A | 4/1972 | Strickler |
| 3,663,395 A | 5/1972 | Strickler |
| 3,668,107 A | 6/1972 | Lappe |
| 3,755,132 A | 8/1973 | Kolin et al. |
| 3,758,395 A | 9/1973 | Strickler |
| 3,821,102 A | 6/1974 | Fletcher et al. |
| 3,847,773 A | 11/1974 | Snyder |
| 3,989,613 A | 11/1976 | Gritzner |
| 4,043,895 A | 8/1977 | Gritzner |
| 4,061,560 A | 12/1977 | Hannig et al. |
| 4,107,027 A | 8/1978 | Muckenmuller et al. |
| 4,141,809 A | 2/1979 | Aitchison et al. |
| 4,204,929 A | 5/1980 | Bier |
| 4,214,981 A | 7/1980 | Giddings |
| 4,310,408 A | 1/1982 | Rose et al. |
| 4,358,358 A | 11/1982 | Rhodes |
| 4,362,612 A | 12/1982 | Bier |
| 4,383,905 A | 5/1983 | Richman |
| 4,394,246 A | 7/1983 | Richman et al. |
| 4,440,638 A | 4/1984 | Judy et al. |
| 4,465,582 A | 8/1984 | Richman |
| 4,749,458 A | 6/1988 | Muroi et al. |
| 4,874,507 A | 10/1989 | Whitlock |
| 4,897,169 A | 1/1990 | Bier et al. |
| 5,032,247 A | 7/1991 | Tarnopolsky |
| 5,071,536 A | 12/1991 | Ivory |
| 5,087,338 A | 2/1992 | Perry et al. |
| 5,131,994 A | 7/1992 | Shmidt et al. |
| 5,133,844 A | 7/1992 | Stevens |
| 5,180,480 A | 1/1993 | Manz |
| 5,277,774 A | 1/1994 | Shmidt et al. |
| 5,336,387 A | 8/1994 | Egen et al. |
| 5,439,571 A | 8/1995 | Sammons et al. |
| 5,447,612 A | 9/1995 | Bier et al. |
| 5,540,826 A | 7/1996 | Bier et al. |
| 5,562,812 A | 10/1996 | Carlson et al. |
| 5,906,724 A | 5/1999 | Sammons et al. |
| 5,972,190 A | 10/1999 | Richman |
| 6,210,574 B1 | 4/2001 | Sammons et al. |
| 6,328,868 B1 | 12/2001 | Weber |
| 6,749,733 B1 | 6/2004 | Sibbett |
| 6,758,953 B2 | 7/2004 | Thomas et al. |
| 6,793,791 B2 | 9/2004 | Bier |
| 2001/0040095 A1 | 11/2001 | Shimizu et al. |
| 2001/0040096 A1 | 11/2001 | Yamamoto et al. |
| 2002/0008027 A1 | 1/2002 | Rhodes et al. |
| 2004/0031683 A1 | 2/2004 | Eipel et al. |
| 2004/0045826 A1 | 3/2004 | Weber |
| 2004/0050697 A1 | 3/2004 | Eckerskorn et al. |
| 2004/0050698 A1 | 3/2004 | Eckerskorn et al. |
| 2004/0101973 A1 | 5/2004 | Weber |
| 2004/0163956 A1 | 8/2004 | Bier |

FOREIGN PATENT DOCUMENTS

| | | |
|---|---|---|
| JP | 061162741 A | 1/1985 |
| JP | 061215952 A | 3/1985 |
| JP | 061215953 A | 3/1985 |
| JP | 063067557 A | 9/1986 |
| JP | 063117252 A | 11/1986 |
| JP | 06130035 A | 5/1994 |
| JP | 2001091497 A | 9/1999 |
| JP | 2001153841 A | 11/1999 |
| JP | 2003247980 A | 2/2002 |
| JP | 2004113079 A | 9/2002 |
| WO | 9110129 | 12/1989 |
| WO | 2004077039 | 9/2004 |

OTHER PUBLICATIONS

Bondy, B., et al., "Sodium chloride in separation medium enhances cell compatibility of free flow electrophoresis", Electrophoresis, vol. 16, 1995, p. 92-97.*

Application Manual for BD(tm) Free Flow Electrophoresis System, Document Revision 4.0, Jul. 2005.*

Operating Manual for BD(tm) Free Flow Electrophoresis System, Document Revision 2.0, Jul. 2005.*

* cited by examiner

METHOD FOR ELECTROPHORESIS INVOLVING PARALLEL AND SIMULTANEOUS SEPARATION

BACKGROUND OF THE INVENTION

1. Field of the Invention

The present invention relates to an electrophoresis method involving parallel and simultaneous separation.

2. Description of Related Art

Since the principle of the method known as free-flow electrophoresis (FFE) was described in DE 805 399, Barrolier, J. et al. in Z. Naturforschung, 1958, 13B, pages 754 to 755, Hannig, K. in Zeitschrift der Analytischen Chemie, 1961, 181, pages 244 to 254 and Roman, M. et al. in Journal of Chromatography 1992, 592, pages 3 to 12 this technique has found a permanent position among efficient analytical and preparative methods used in industry and chemistry. Although both small ions as well as large particles can be separated using this technique, a major application is the fractionation of proteins, especially in the biotechnological production of enzymes and other biologically active proteins, membrane particles and even viable cells. In comparison to other methods enabling isolation of separated sample components, FFE offers two main advantages: (i) the separation may be performed continuously and enables one to obtain as much as hundreds of milligrams or even gram amounts of pure substances per hour and (ii) the separation is gentle and preserves enzymatic activity of the separated components. The technology of FFE is particularly useful in the separation and fractionation of complex proteins, and is thus applicable to the emergent field of proteomics, which is growing increasingly important in the academic research, pharmaceutical, biotechnology and clinical diagnostic markets. For example, as proteomic research has grown, there has been an increased demand in the improvement of protein separation performance, especially relative to resolution process reliability, and a universal front-end.

Generally, free-flow separation methods are suitable for separating ions of any molecular weight as well as bioparticles. It generally does not matter whether the sample to be separated is itself electrically charged or whether the charge is generated by the adsorption or sorption of ions. The process of continuous deflection electrophoresis and its improvement by way of stabilization media and counter-flow media is reflected, for example, in U.S. Pat. No. 5,275,706, the disclosure of which is hereby incorporated by reference. According to this patent, the counter-flow medium is introduced into the separation space counter to the flow direction of the separation medium. Both media are discharged through fractionation outlets, resulting in a fractionation having a low void volume and, additionally, maintaining a laminar flow of the media in the region of the fractionation outlets, e.g., with very low turbulence. A discussion of various modes of free flow electrophoresis can be found, for example, in U.S. patent application 2004/0050697, the disclosure of which is hereby incorporated by reference.

Isoelectric focusing is an electrophoretic technique that adds a pH-gradient to the buffer solution and together with the electric field focuses most biological materials that are amphoteric. Amphoteric biomaterials such as proteins, peptides, and, viruses, are positively charged in acidic media and negatively charged in basic media. During IEF, these materials migrate in the pH-gradient that is established across, i.e., transverse to the flow-direction, to their isoelectric point (pI) where they have no net charge and form stable, narrow zones. At this point the materials stop migrating transversely and they become focused. In this technique, there is no voltage dependence. Isoelectric focusing yields such high resolution bands because any amphoteric biomaterial which moves away from its isoelectric point due to diffusion or fluid movement will be returned by the combined action of the pH gradient and electric field. The focusing process thus purifies and concentrates the samples into bands that are relatively stable. This is a powerful concept that has yielded some of the highest resolution separations, especially when coupled with electrophoresis in two-dimensional gels.

Zone electrophoresis is another separation mode that can be used in FFE. Zone electrophoresis separates bioparticles primarily based on charge, and to a lesser extent form and size. A further mode that can be used in FFE is isotachophoresis (ITP). ITP FFE involves use of a non-homogeneous separation media. When components separate from the main band of the initial sample, the components enter an area when they are accelerated or decelerated transverse to the bulk sample flow, based on the local conditions. This so-called focusing effect is then used to fractionate the desired components from the bulk sample.

Typically, FFE methods involve separation, by flowing the sample through a single separation space within a chamber, this space flanked by two electrodes. An improved method, allowing parallel and simultaneous focusing, in a single chamber, is reflected in United States patent application US2004/045826. This patent application describes a single separation chamber with multiple electrodes, to provide multiple separation spaces within a single chamber. Further improvements relating to parallel, simultaneous separation within a single chamber are desired.

SUMMARY OF THE INVENTION

In one embodiment, the invention provides a method comprising the steps of:

(a) providing a separation chamber comprising a first end wall, a second end wall, a first sidewall, a second side wall, and two plates, wherein the end walls, sidewalls and plates define a separation space; a single anode and a single cathode located in the separation chamber in proximity to the first sidewall and the second sidewall, respectively; at least two sample inlets located in proximity to the first end wall; at least two separation medium inlets located in proximity to the first end wall; a first anodic stabilization medium inlet in proximity to the first end wall and in proximity to the anode; a first cathodic stabilization medium inlet in proximity to the first end wall and in proximity to the cathode; and one or more additional anodic stabilization medium inlets and one or more additional cathodic stabilization medium inlets, the additional anodic and cathodic stabilization medium inlets located in proximity to the first end wall and further located between the first anodic stabilization medium inlet and the first cathodic stabilization medium inlet, (b) introducing at least one separation medium through the at least two separation medium inlets into the separation chamber, (c) introducing one or more samples to be separated through the at least two sample inlets into the separation chamber, and (d) introducing an anodic stabilization medium through the first and the additional anodic stabilization medium inlets into the separation chamber and introducing a cathodic stabilization medium through the first and the additional cathodic stabilization medium inlets into the separation chamber, wherein one or more boundaries defining separation sub-spaces are provided by adjacent flow of anodic and cathodic stabilization media through the additional anodic stabilization medium inlets and the additional cathodic stabilization medium inlets.

In a further embodiment, the invention provides a method comprising the steps of:

(a) providing a separation chamber comprising a first end wall, a second end wall, a first sidewall, a second side wall, and two plates, wherein the end walls, sidewalls and plates define a separation space; an anode and a cathode located in the separation chamber in proximity to the first sidewall and the second sidewall, respectively; at least two sample inlets located in proximity to the first end wall; at least two separation medium inlets located in proximity to the first end wall; a first anodic stabilization medium inlet in proximity to the first end wall and in proximity to the anode; a first cathodic stabilization medium inlet in proximity to the first end wall and in proximity to the cathode; and one or more additional anodic stabilization medium inlets and one or more additional cathodic stabilization medium inlets, the additional anodic and cathodic stabilization medium inlets located in proximity to the first end wall and further located between the first anodic stabilization medium inlet and the first cathodic stabilization medium inlet, (b) introducing at least one separation medium through the at least two separation medium inlets into the separation chamber, (c) introducing one or more samples to be separated through the at least two sample inlets into the separation chamber, and (d) introducing an anodic stabilization medium through the first and the additional anodic stabilization medium inlets into the separation chamber and introducing a cathodic stabilization medium through the first and the additional cathodic stabilization medium inlets into the separation chamber, wherein one or more boundaries defining separation sub-spaces are provided by adjacent flow of anodic and cathodic stabilization media through the additional anodic stabilization medium inlets and the additional cathodic stabilization medium inlets, wherein the anodic stabilization medium comprises a monoprotic acid the anion of which has an electrophoretic mobility less than or equal to about 40 m$^2$/V/sec, and wherein the cathodic stabilization medium comprises a monobasic base the cation of which has an electrophoretic mobility less than or equal to about 40 m$^2$/V/sec.

These embodiments also involve generating an electric field via the anode and cathode. The separation sub-spaces allow parallel and simultaneous separation within the overall device, each sub-space essentially acting as an independent separation chamber. The invention is therefore able to provide, for example, separation of an increased amount of sample via parallel and simultaneous processes, yet without the need for multiple, separate chambers and instruments.

(In both embodiments above, one or more of the introducing and generating steps may be performed simultaneously, or in a different order than as presented above.)

DETAILED DESCRIPTION

Figure 1:
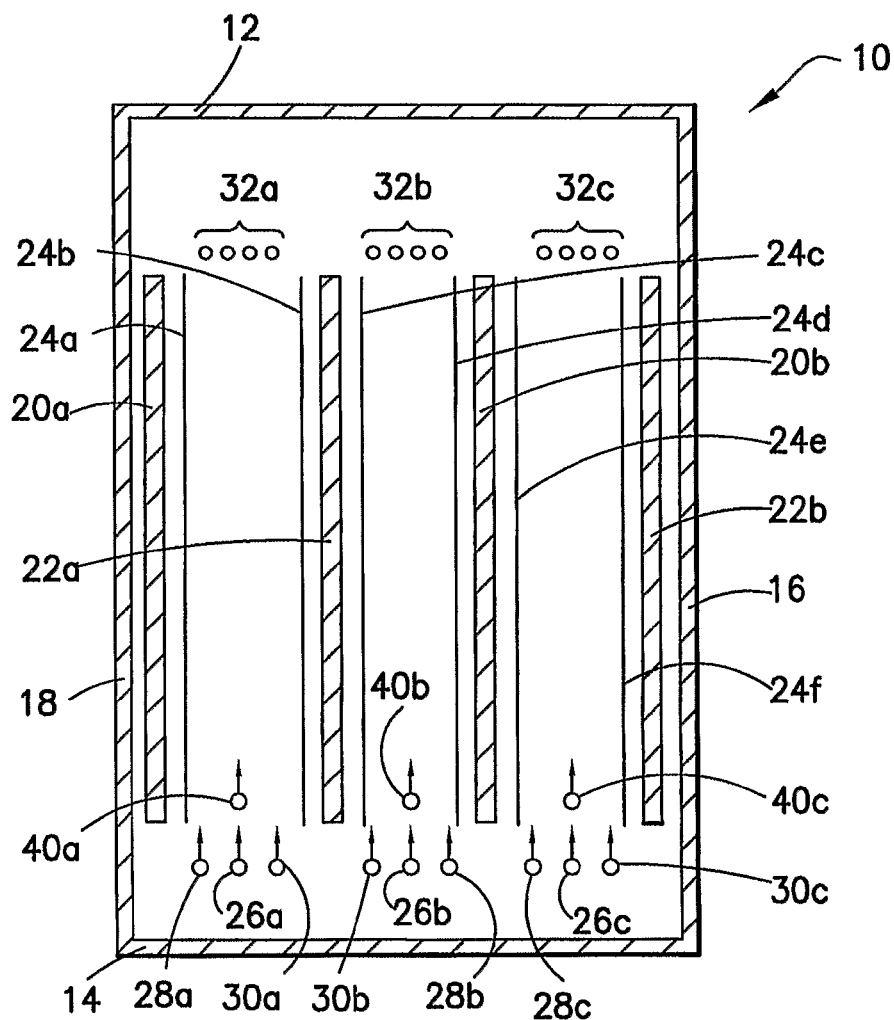
FIG. 1 is a schematic view of a prior art apparatus for performing parallel and simultaneous carrier-free electrophoresis, comprising three separation spaces, each space defined by two electrodes.

FIG. 1 shows a separation chamber 10 according to the prior art which is sub-divided into three separation spaces, each being flanked by an anode and a cathode (i.e., electrode pairs of anode 20a and cathode 22a, cathode 22a and anode 20b, and anode 20b and cathode 22b). (Electrode membranes 24a-24f are also provided.) Each separation space contains: a sample inlet 40a, 40b, 40c; an anodic stabilization medium inlet 28a, 28b, 28c; a cathodic stabilization medium inlet 30a, 30b, 30c; and a separation medium inlet 26a, 26b, 26c. Thus, the separation chamber defined by first end wall 14, second end wall 12, and sidewalls 16 and 18 and two parallel plates (not shown), contains three separation sub-spaces that allow three separations to occur simultaneously. In each sub-space, portions of the injected sample are separated in the direction transverse to the flow direction, based on, for example, their isoelectric point, as discussed above. The separated fractions are collected through collection outlets 32a, 32b, 32c arranged in proximity to the second end wall. The analytes that are typically collected are led through individual tubings to individual collection vessels, walls, microfiter plates, or the like (not shown). The chamber is typically rectangular in shape, with the end walls 12, 14 and side walls 16, 18 forming a rectangle and supporting opposed parallel plates closely spaced to form a separation space. The electrodes are arranged parallel to the side walls within the chamber.

According to embodiments of the invention, it is possible to generate a plurality of separation sub-spaces between a single anode and single cathode. The embodiments below relate to a separation chamber having a single anode and cathode, but it is possible, for example, to have multiple anodes and cathodes, with multiple separation sub-spaces between each anode-cathode pair.

Figure 2:
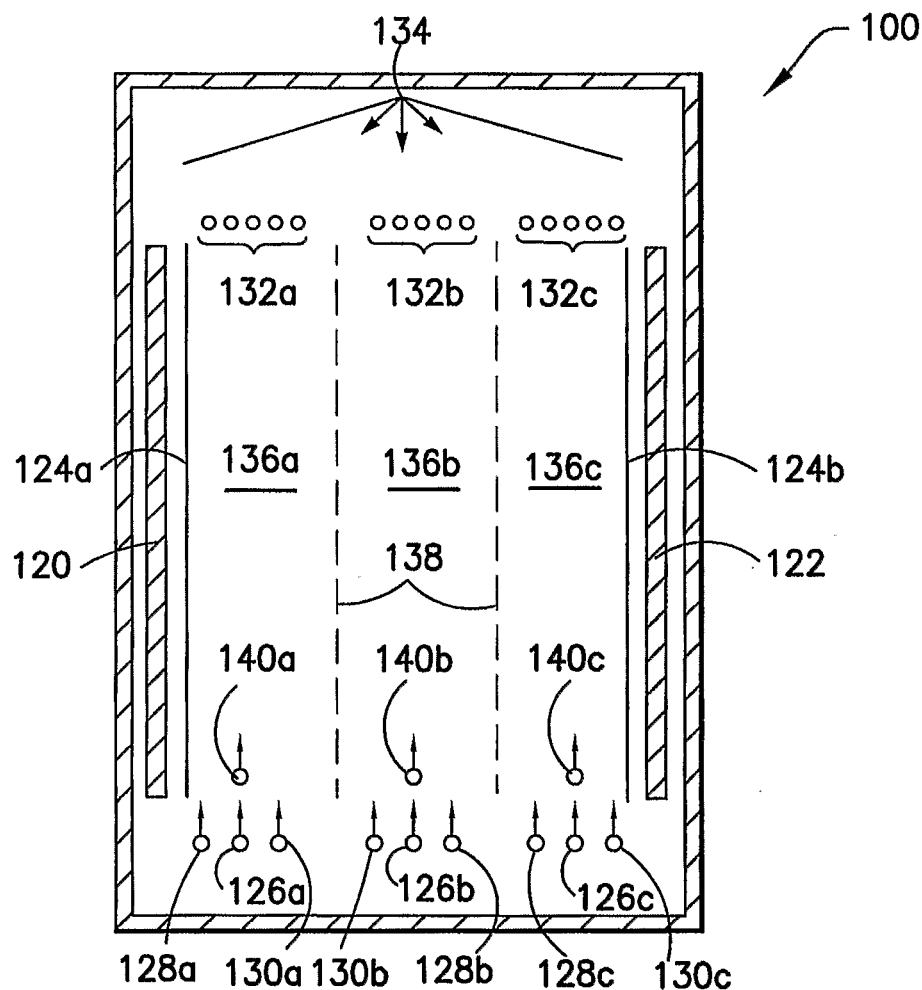
FIG. 2 is a schematic view of an embodiment of the invention.

FIG. 2 schematically shows a separation chamber 100 for carrying out a parallel and simultaneous carrier-free separation according to an embodiment of the invention. The separation chamber 100 is configured similarly to the prior art chamber, but contains only a single anode 120 and a single cathode 122 arranged in parallel at opposing sidewalls of the chamber 100. The separation space in the chamber is sub-divided into three individual separation sub-spaces 136a-136c, with boundaries identified by element 138. Each sub-space is provided with a sample inlet 140a-140c, a separation medium inlet 126a-126c, an anodic stabilization medium inlet 128a-128b, and a cathodic stabilization medium inlet 130a-130c. Separated fraction outlets 132a-132c are also provided. The direction of flow from the inlets is shown by the arrows.

As discussed in more detail below, the boundaries 138 between adjacent sub-spaces are defined by the adjacent flows of cathodic stabilization medium and anodic stabilization medium, e.g., from inlets 130a and 128b, and inlets 130b and 128c. All media are typically introduced through their respective inlets via a pump such as a multi-channel peristaltic pump. The electrode membranes 124a and 124b are typically electrically conductive, and separate the electrode space from the separation space to prevent exchange of media caused by hydrodynamic flow. (The membranes are typically located very close to the electrode, but for clarity the drawings show the membranes spaced from the electrodes.)

The method of the above embodiment is capable of providing a two-electrode separation chamber with x individual separation sub-spaces being flanked by x+1 electrode stabilization media flows. According to one embodiment, to generate s separation sub-spaces within the separation chamber, s−1 pairs of adjacent anode/cathode stabilization medium inlets are provided, at least s inlets for the injection of the sample are provided, at least s separation medium inlets are provided, and at least s, typically at least 3 s, fractionation outlets are provided. Depending on the dimensions of the separation chamber, the number of created separation sub-spaces s may be from 2 to 7. As is apparent, the number of pumps for the introduction of the sample, separation medium and electrodic stabilization media and the number of channels comprised in each pump is adjusted accordingly.

According to embodiments of the invention, cross-contamination between different separation sub-spaces (e.g., contamination across boundary 138) can be reduced by selection of monoprotic acids and monobasic bases for the anodic and cathodic media. It is generally useful to provide such acids and bases having high molecular weight and low electrophoretic mobility.

In particular, according to one embodiment, monoprotic acids and monobasic bases of the anodic and cathodic media have a molecular weight of at least about 100, and in another embodiment a range of about 150 to about 300. In another embodiment, the useful concentration for both the monoprotic acid and the monobasic base (the concentrations of which are independent from each other) is at least about 50 mmol/liter.

According to another embodiment, the anodic stabilization medium contains a monoprotic acid the anion of which has an electrophoretic mobility≤about $40\times10^{-9}$ m$^2$/V/sec, and the cathodic stabilization medium contains a monobasic base the cation of which has an electrophoretic mobility≤about $40\times10^{-9}$ m$^2$/V/sec. In a further embodiment, the electrophoretic mobility of such an anion and such a cation is from about $25\times10^{-9}$ m$^2$/V/sec to about $30\times10^{-9}$ m$^2$/V/sec.

Electrophoretic mobility (EM), as used herein, means the rate of migration of anions and cations in an electrical field at a given field strength per time unit in an aqueous media. The electrophoretic mobility u can be calculated as follows:

$$u = s/H \times t$$

wherein s represents the distance of migration (m), H represents the electric field strength (V/m) and t represents the time (sec.).

In some embodiments of the invention, the anodic stabilization medium, which is typically aqueous, contains an acid selected from the group consisting of gluconic acid, glucuronic acid, acetylsalicylic acid, 2-(N-morpholino) ethanesulphonic acid (MES), and zwitterionic buffers (also called Goods buffers—see Good et al., *Biochemistry* 5, 467 (1966)). In some embodiments of the invention, the cathodic stabilization medium, which is typically aqueous, contains a base selected from the group consisting of N-methyl-D-glucosamine, tri-isopropanolamine and 2-[bis(2-hydroxyethyl) amino]-2-(hydroxymethyl)propane-1,3-diol (BISTRIS).

Figure 3:
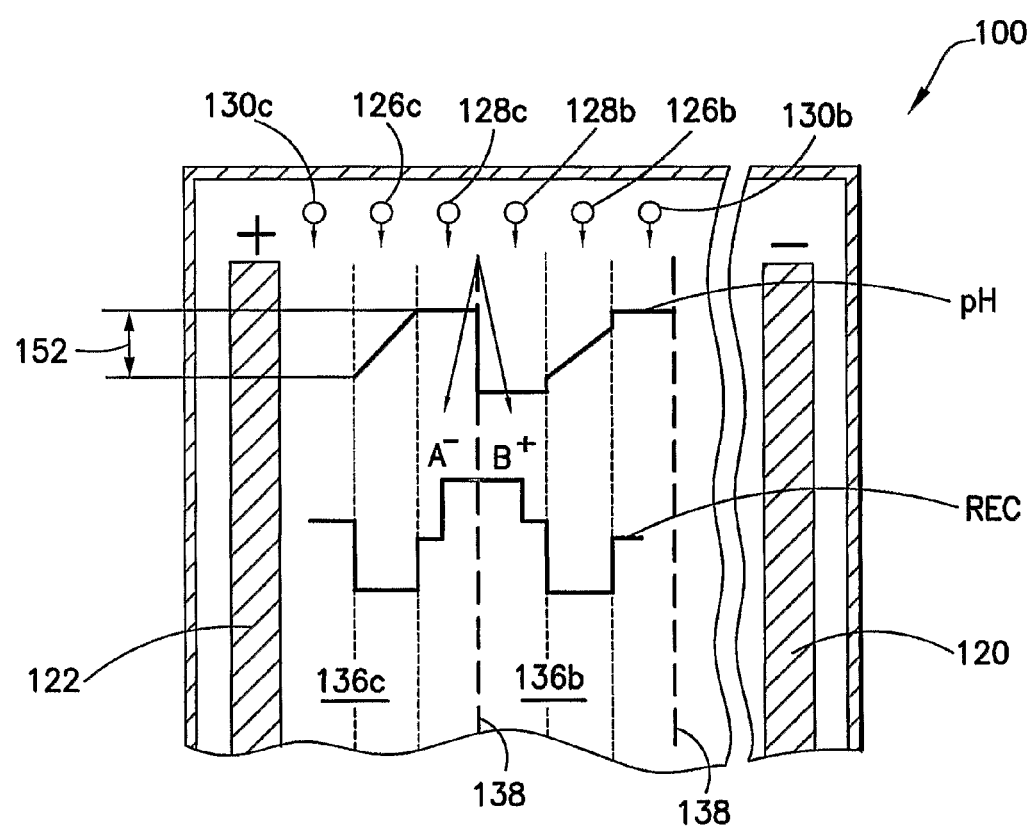
FIG. 3 demonstrates the characteristics of the free flow electrophoresis chamber according to an embodiment of the invention.

The effect of the process reflected in FIG. 2 is shown in FIG. 3, which shows aspects of separation sub-spaces 136b and 136c. The heavy dashed lines 138 depict the boundaries between sub-spaces, with lighter dashes showing flow paths of media from the various inlets. The term REC denotes the relative electric conductivity of the media. FIG. 3 shows the anode 120 and the cathode 122. Anodic stabilization medium is introduced through inlets 128b and 128c, cathodic stabilization medium is introduced through inlets 130b and 130c, and separation medium is introduced through inlets 126b and 126c, with flow being in the direction shown by the arrows.

As reflected in FIG. 3, cross-over of the cation (B+) of the cathodic stabilization medium and the anion (A$^-$) past the boundary between spaces 136a and 136b (between adjacent flows of anodic and cathodic separation media) is controlled, thereby maintaining integrity of the individual separation sub-spaces. In particular, selection of monoprotic acids and bases with anions and cations of relatively low electrophoretic mobilities, as discussed above, reduce the cross-over.

In addition, as reflected in the REC plot in FIG. 3, the relative electrical conductivity of the media can also contribute to the integrity of the separation sub-spaces. In one embodiment, the electrical conductivity of the anodic and cathodic stabilization media from inlets 128c and 130c is at least 5 times the electrical conductivity of the separation medium from inlet 126c, and contributes to maintaining the sample flow within the separation medium. However, as higher electrical conductivity stabilization media are selected, it is possible to encounter higher heat dissipation and increased density and viscosity (and thus lower flow rate). Thus, a balance between the various parameters and considerations is generally made.

In the case of IEF mode, it is useful to select media with specific pH values, to facilitate separation of the component of interest. Generally, the pH values are selected based on the isoelectric point of the component or components of interest, to ensure the component(s) are properly separated. It is useful in some embodiments to provide an anodic stabilization medium having a pH about 0.5 to about 3 pH units less than the pH of the lowest-pH constituent of the separation medium. It is similarly useful to provide a cathodic stabilization medium having a pH about 0.5 to about 3 pH units higher than the pH of the highest-pH constituent of the separation medium. In some embodiments, these ranges are about 0.8 to about 2 pH units. In the embodiment reflected in FIG. 3, for sub-space 136c, a pH gradient 152 is created across the separation medium from inlet 126c, between the cathodic stabilization medium from inlet 130c and the anodic separation medium from inlet 128c. Typically, the pH span of the gradient 152 that occurs across the separation medium can vary between about 0.3 and about 8.5.

Referring again to FIG. 2, at the second end of the separation chamber, the individual separated analytes that flow on distinct paths in each individual separation chamber are collected through collection outlets 132a-132c, which are generally arranged along a line perpendicular to the flow direction. Typically, each separation sub-space contains the same arrangement of collection outlets. If identical samples are being separated and identical fractions are desired, the effluent of collection outlets containing the same analyte from each separation sub-space can be combined.

The individual analytes exit the separation chamber through the multiple collection outlets 132a-132c and are generally led through individual tubing to individual collection vessels of any suitable type. In the collection vessels, the analyte is collected together with the separation medium and counter-flow medium. The distance between the individual collection outlets of the array of collection outlets should generally be as small as possible in order to provide for a suitable fractionation/separation. The distance between individual collection outlets, measured from the centers of the collection outlets, can be from about 0.1 mm to about 2 mm, more typically from about 0.3 mm to about 1.5 mm.

It is possible to use a counterflow in a chamber according to an embodiment of the invention. For example, in FIG. 2, a counter-flow medium is introduced into the separation chamber via counterflow element 134, in a direction opposite the direction in which the sample and separation medium is introduced. The counter-flow enhances separation by allowing adjustment and control of the flow and pressure conditions at the collection outlets 132a-132c.

The counter-flow media is typically selected to be capable of modifying or surpassing the buffering capacity of the separation medium approaching the fractionation outlets, and may therefore be a material having the same viscosity and density but differing in conductivity and/or pH-value and/or their chemical ingredients. Typical counter-flow and separation media are selected from the same group of media, and typically contain components such as urea, glycerol, carbohydrates glucose, and similar compounds. Such media usually contain a mixture of amphoteric substances with varying isoelectric points, such that the individual components become ordered under influence of the electric field in the chamber. These media are commercially available from several sources, e.g., Immobiline™, Ampholine™ and Pharmalyte™ from General Electric, Servalyt™ from SERVA Electrophoresis GmbH, and similar materials from Becton, Dickinson and Company.

A useful ratio of the flow-rate of the separation medium to the flow rate of the counter-flow medium is about 1:10 to about 10:1, more typically about 1:3 to about 3:1. The actual flow rates for the separation medium and the counter-flow media depend on a variety of considerations, including the geometrical dimensions of the instrument, the particular separation mode used (which may vary in required transit time), the sample to be separated, the separation medium used and the counter-flow medium or media used in order to obtain an optimum separation of the analytes. Typical flow rates of all media into the system (stabilization and counter-flow) may therefore range widely from 0.3 mL/hour to 3000 mL/hour.

An apparatus according to embodiments of the invention further comprises a multi-channel pump for the separation medium, a multi-channel pump for the sample, and a multi-channel pump for the counter-flow medium/media. The device further comprises a fraction collector outlet and outlet tubes. Typically, the pumps are multi-channel peristaltic pumps.

According to embodiments of the invention, the method can be combined with variations of free flow electrophoresis processes and devices. For example, multiple devices can be used, which are then arranged in parallel and/or in series. Alternatively, the component flow collected at the collection outlets of a device may be recycled back to the corresponding sample inlets to form a recycling process which can improve resolution by increasing sample component residence time.

The bottom plate and the upper plate of the separation chamber can independently be made of glass, or suitable plastics, such as PVC, polyolefins, polycarbonate, plexiglass, polyhalohydrocarbons, or Lucite® (an acrylic resin consisting essentially of polymerized methyl methacrylate), with polymer coated glass being preferred. The top and bottom plates are typically separated by spacers that act as gaskets or seals.

The electrodes are typically composed of a metal such as platinum that will not easily be oxidized in the electric field. The electrodes are typically separated from the separation chamber by ion-exchange, nylon or cellulose acetate membranes. The electrodes are typically washed constantly by a salt or buffer solution to remove electrolysis products that are created during the process.

The separation space (space between plates) usually has a thickness of about 0.1 to about 1.5 mm, preferably between about 0.3 and about 1.0 mm.

Temperature control is also useful according to embodiments of the invention. When current passes through an electrolyte solution, the temperature of the conduction medium increases, according to the phenomenon known as Joule heating. To reduce disturbances to the laminar flow profile of the flowing medium caused by such heating, it is generally desirable to dissipate the Joule heat to the surroundings. In one embodiment, the separation chamber is arranged with its bottom plate on a metal support that contains fluid flow channels connected to a temperature control device, such as a thermostat system for controlling the temperature of the separating chamber. Useful temperature ranges are about 2° C. and about 35° C., more typically about 5° C. to room temperature (about 25° C.).

The invention is particularly suitable for, but not limited to, the analysis and preparative separation of ions, peptides, biopolymers, bioparticles as well as synthetic polymers and particles.

In addition, various FFE modes are possible, for example, IEF and isotachophoresis. It is contemplated that all sub-spaces within a single chamber could use a single FFE mode, or that different sub-spaces within the same chamber could use differing modes.

The above descriptive embodiments are only exemplary of the present invention, and there are numerous modifications and alternative modes that would fall within the scope of the invention, which is set forth in the claims appended hereto.

What is claimed is:

1. A method for electrophoresis, comprising the steps of:
   (a) providing a separation chamber comprising a first end wall, a second end wall, a first sidewall, a second side wall, and two plates, wherein the end walls, sidewalls and plates define a separation space; a single anode and a single cathode located in the separation chamber in proximity to the first sidewall and the second sidewall, respectively; at least two sample inlets located in proximity to the first end wall; at least two separation medium inlets located in proximity to the first end wall; a first anodic stabilization medium inlet in proximity to the first end wall and in proximity to the anode; a first cathodic stabilization medium inlet in proximity to the first end wall and in proximity to the cathode; and one or more additional anodic stabilization medium inlets and one or more additional cathodic stabilization medium inlets, the additional anodic and cathodic stabilization medium inlets located in proximity to the first end wall and further located between the first anodic stabilization medium inlet and the first cathodic stabilization medium inlet;
   (b) introducing at least one separation medium through the at least two separation medium inlets into the separation chamber;
   (c) introducing one or more samples to be separated through the at least two sample inlets into the separation chamber;
   (d) generating an electric field via the anode and cathode; and
   (e) introducing an anodic stabilization medium through the first and the additional anodic stabilization medium inlets into the separation chamber and introducing a cathodic stabilization medium through the first and the additional cathodic stabilization medium inlets into the separation chamber, wherein one or more boundaries defining separation sub-spaces are provided by adjacent flow of anodic and cathodic stabilization media through the additional one or more additional anodic stabilization medium inlets and the one or more additional cathodic stabilization medium inlets.

2. The method of claim 1, further comprising the step of introducing a counter-flow medium into each separation subspace from one or more counterflow inlets located in proximity to the second wall of the separation chamber.

3. The method of claim 1, wherein the first and second end walls, the first and second sidewalls and the two plates define a rectangular chamber.

4. The method of claim 3, wherein the anode and cathode are located substantially parallel to the first and second sidewalls.

5. The method of claim 1, wherein the chamber further comprises a plurality of collection outlets located in proximity to the second end wall.

6. The method of claim 1, wherein the one or more samples are separated by isoelectric focusing.

* * * * *

UNITED STATES PATENT AND TRADEMARK OFFICE
CERTIFICATE OF CORRECTION

PATENT NO. : 8,721,861 B2  Page 1 of 1
APPLICATION NO. : 11/912612
DATED : May 13, 2014
INVENTOR(S) : Gerhard Weber It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1573 days.

Signed and Sealed this

Twenty-ninth Day of September, 2015

Michelle K. Lee
*Director of the United States Patent and Trademark Office*